United States Patent
Baker, Jr.

(10) Patent No.: US 8,423,109 B2
(45) Date of Patent: *Apr. 16, 2013

(54) METHOD FOR ENHANCING PULSE OXIMERY CALCULATIONS IN THE PRESENCE OF CORRELATED ARTIFACTS

(75) Inventor: Clark R. Baker, Jr., Castro Valley, CA (US)

(73) Assignee: Covidien LP, Mansfield, MA (US)

( * ) Notice: Subject to any disclaimer, the term of this patent is extended or adjusted under 35 U.S.C. 154(b) by 1335 days.

This patent is subject to a terminal disclaimer.

(21) Appl. No.: 12/143,358

(22) Filed: Jun. 20, 2008

(65) Prior Publication Data

US 2008/0255436 A1   Oct. 16, 2008

Related U.S. Application Data

(63) Continuation of application No. 11/072,682, filed on Mar. 3, 2005, now Pat. No. 7,392,075.

(51) Int. Cl.
*A61B 5/1455* (2006.01)
(52) U.S. Cl.
USPC ............ 600/336; 600/323; 600/324; 600/331
(58) Field of Classification Search .................. 600/310, 600/322, 323, 324, 331, 336, 502
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |

(Continued)

FOREIGN PATENT DOCUMENTS

| | | |
|---|---|---|
| DE | 19640807 | 9/1997 |
| EP | 0630203 | 12/1994 |

(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

(Continued)

*Primary Examiner* — Eric Winakur

(57) ABSTRACT

A method for determining a physiological parameter in the presence of correlated artifact, including obtaining two digital waveforms, x and y, the waveforms being representative of the absorption of two wavelengths of electromagnetic energy received from a blood-perfused tissue, and where each of the waveforms has a component corresponding to a plethysmographic waveform and a component corresponding to the correlated artifact; calculating several weighted difference waveforms of the form x−R*y, where R is a multiplier, by varying R over a range; evaluating the several weighted difference waveforms using a shape characteristic of the weighted difference waveform; identifying a weighted difference waveform most closely representative of and one most different from the plethysmographic waveform; determining a pleth-based physiological parameter using the waveform most closely representative of the plethysmographic waveform; determining at least one artifact-based physiological parameter using the waveform most different from the plethysmographic waveform; and rejecting other possible candidate values for the pleth-based physiological parameter using the artifact-based physiological parameter.

20 Claims, 5 Drawing Sheets

U.S. PATENT DOCUMENTS

| | | | |
|---|---|---|---|
| 4,934,372 A | 6/1990 | Corenman et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 5,025,791 A | 6/1991 | Niwa |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,226,417 A | 7/1993 | Swedlow et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,355,880 A | 10/1994 | Thomas et al. |
| 5,355,882 A | 10/1994 | Ukawa et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| RE35,122 E | 12/1995 | Corenman et al. |
| 5,482,036 A | 1/1996 | Diab et al. |
| 5,483,646 A | 1/1996 | Uchikoga |
| 5,485,847 A | 1/1996 | Baker, Jr. |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Kuenstner |
| 5,730,124 A | 3/1998 | Yamauchi |
| 5,743,263 A | 4/1998 | Baker, Jr. |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | Delonzor et al. |
| 5,830,139 A | 11/1998 | Abreu |
| 5,831,598 A | 11/1998 | Kauffert et al. |
| 5,842,981 A | 12/1998 | Larsen et al. |
| 5,853,364 A | 12/1998 | Baker, Jr. et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,924,980 A | 7/1999 | Coetzee |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,081,742 A | 6/2000 | Amano et al. |
| 6,083,172 A | 7/2000 | Baker, Jr. et al. |
| 6,088,607 A | 7/2000 | Diab et al. |
| 6,094,592 A | 7/2000 | Yorkey et al. |
| 6,120,460 A | 9/2000 | Abreu |
| 6,134,460 A | 10/2000 | Chance |
| 6,135,952 A | 10/2000 | Coetzee |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,397,091 B2 | 5/2002 | Diab et al. |
| 6,408,198 B1 | 6/2002 | Hanna et al. |
| 6,411,833 B1 | 6/2002 | Baker, Jr. et al. |
| 6,415,236 B2 | 7/2002 | Kobayashi et al. |
| 6,419,671 B1 | 7/2002 | Lemberg |
| 6,430,525 B1 | 8/2002 | Weber et al. |
| 6,438,399 B1 | 8/2002 | Kurth |
| 6,461,305 B1 | 10/2002 | Schnall |
| 6,463,311 B1 * | 10/2002 | Diab ........................ 600/324 |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,505,060 B1 | 1/2003 | Norris |
| 6,510,329 B2 | 1/2003 | Heckel |
| 6,519,486 B1 | 2/2003 | Edgar, Jr. et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,574,491 B2 | 6/2003 | Elghazzawi |
| 6,580,086 B1 | 6/2003 | Schulz et al. |
| 6,591,122 B2 | 7/2003 | Schmitt |
| 6,594,512 B2 | 7/2003 | Huang |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,721,584 B2 | 4/2004 | Baker, Jr. |
| 6,731,274 B2 | 5/2004 | Powell |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,810,277 B2 | 10/2004 | Edgar, Jr. et al. |
| 6,816,741 B2 | 11/2004 | Diab |
| 6,829,496 B2 | 12/2004 | Nagai et al. |
| 6,836,679 B2 | 12/2004 | Baker, Jr. et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,930,608 B2 | 8/2005 | Grajales et al. |
| 6,931,269 B2 | 8/2005 | Terry |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,016,715 B2 * | 3/2006 | Stetson ........................ 600/336 |
| 7,024,233 B2 | 4/2006 | Ali |
| 7,024,235 B2 | 4/2006 | Melker et al. |
| 7,027,849 B2 | 4/2006 | Al-Ali |
| 7,030,749 B2 | 4/2006 | Al-Ali |
| 7,035,679 B2 | 4/2006 | Addison et al. |
| 7,035,697 B1 | 4/2006 | Brown |

| | | | |
|---|---|---|---|
| 7,039,538 B2 | 5/2006 | Baker, Jr. | |
| 7,044,918 B2 | 5/2006 | Diab | |
| 7,047,056 B2 | 5/2006 | Hannula et al. | |
| 7,072,702 B2 | 7/2006 | Edgar, Jr. et al. | |
| 7,127,278 B2 | 10/2006 | Melker et al. | |
| 7,162,306 B2 | 1/2007 | Caby et al. | |
| 7,194,293 B2 | 3/2007 | Baker, Jr. et al. | |
| 7,209,774 B2 | 4/2007 | Baker, Jr. | |
| 7,209,775 B2 | 4/2007 | Bae et al. | |
| 7,215,984 B2 | 5/2007 | Diab et al. | |
| 7,215,986 B2 | 5/2007 | Diab et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,302,284 B2 | 11/2007 | Baker, Jr. et al. | |
| 7,315,753 B2 | 1/2008 | Baker, Jr. et al. | |
| 7,328,053 B1 | 2/2008 | Diab et al. | |
| 7,336,982 B2 | 2/2008 | Yoo | |
| 7,336,983 B2 | 2/2008 | Baker, Jr. et al. | |
| 7,373,193 B2 | 5/2008 | Al-Ali et al. | |
| 7,376,453 B1 | 5/2008 | Diab et al. | |
| 7,383,070 B2 | 6/2008 | Diab et al. | |
| 7,474,907 B2 | 1/2009 | Baker, Jr. | |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0097049 A1 | 5/2003 | Diab et al. | |
| 2003/0139687 A1 | 7/2003 | Abreu | |
| 2003/0144584 A1 | 7/2003 | Mendelson | |
| 2003/0187337 A1 | 10/2003 | Tarassenko et al. | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0158135 A1 | 8/2004 | Baker, Jr. et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0181134 A1 | 9/2004 | Baker, Jr. et al. | |
| 2004/0204636 A1 | 10/2004 | Diab et al. | |
| 2004/0230106 A1 | 11/2004 | Schmitt et al. | |
| 2005/0033129 A1 | 2/2005 | Edgar, Jr. et al. | |
| 2005/0049470 A1 | 3/2005 | Terry | |
| 2005/0080323 A1 | 4/2005 | Kato | |
| 2005/0085735 A1 | 4/2005 | Baker, Jr. et al. | |
| 2005/0101850 A1 | 5/2005 | Parker | |
| 2005/0113651 A1 | 5/2005 | Wood et al. | |
| 2005/0113656 A1 | 5/2005 | Chance | |
| 2005/0143634 A1 | 6/2005 | Baker, Jr. et al. | |
| 2005/0168722 A1 | 8/2005 | Forstner et al. | |
| 2005/0177034 A1 | 8/2005 | Beaumont | |
| 2005/0192488 A1 | 9/2005 | Bryenton et al. | |
| 2005/0197552 A1 | 9/2005 | Baker, Jr. | |
| 2005/0197793 A1 | 9/2005 | Baker, Jr. | |
| 2005/0203357 A1 | 9/2005 | Debreczeny et al. | |
| 2005/0209517 A1 | 9/2005 | Diab et al. | |
| 2005/0228248 A1 | 10/2005 | Dietiker | |
| 2005/0267346 A1 | 12/2005 | Faber et al. | |
| 2005/0283059 A1 | 12/2005 | Iyer et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0064024 A1 | 3/2006 | Schnall | |
| 2006/0122476 A1 | 6/2006 | Van Slyke | |
| 2006/0161389 A1 | 7/2006 | Weber et al. | |
| 2006/0195025 A1 | 8/2006 | Ali et al. | |
| 2006/0195028 A1 | 8/2006 | Hannula et al. | |
| 2006/0195280 A1 | 8/2006 | Baker, Jr. | |
| 2006/0206021 A1 | 9/2006 | Diab | |
| 2006/0217609 A1 | 9/2006 | Diab et al. | |
| 2006/0224058 A1 | 10/2006 | Mannheimer | |
| 2006/0247501 A1 | 11/2006 | Ali | |
| 2006/0258921 A1 | 11/2006 | Addison et al. | |
| 2006/0258927 A1 | 11/2006 | Edgar, Jr. et al. | |
| 2007/0213621 A1 | 9/2007 | Reisfeld et al. | |
| 2007/0225581 A1 | 9/2007 | Diab et al. | |
| 2007/0249918 A1 | 10/2007 | Diab et al. | |
| 2007/0291832 A1 | 12/2007 | Diab et al. | |
| 2008/0004514 A1 | 1/2008 | Diab et al. | |
| 2008/0033266 A1 | 2/2008 | Diab et al. | |
| 2008/0045823 A1 | 2/2008 | Diab et al. | |

FOREIGN PATENT DOCUMENTS

| | | |
|---|---|---|
| EP | 1006863 | 10/2003 |
| EP | 1006864 | 10/2003 |
| EP | 1491135 | 12/2004 |
| JP | 3170866 | 7/1991 |
| JP | 3238813 | 10/1991 |
| JP | 4191642 | 7/1992 |
| JP | 4332536 | 11/1992 |
| JP | 7124138 | 5/1995 |
| JP | 7136150 | 5/1995 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 | 7/2004 |
| JP | 2004202190 | 7/2004 |
| JP | 2004248819 | 9/2004 |
| JP | 2004290545 | 10/2004 |
| WO | WO9101678 | 2/1991 |
| WO | WO9221281 | 12/1992 |
| WO | WO9309711 | 5/1993 |
| WO | WO9403102 | 2/1994 |
| WO | WO9512349 | 5/1995 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO0125802 | 4/2001 |
| WO | WO03000125 | 1/2003 |
| WO | WO2004075746 | 9/2004 |
| WO | WO2005009221 | 2/2005 |

OTHER PUBLICATIONS

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Kaestle, S.; "An Algorithm for Reliable Processing of Pulse Oximetry Signals Under strong Noise Conditions," *Dissertation Book*, Lubeck University, Germany (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2000).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 2004, pp. 2153-2156.

Matsuzawa, Y., et al.; "Pulse Oximeter," *Home Care Medicine*, pp. 42-45 (Jul. 2004); (Article in Japanese—contains English summary of article).

Yan, Yong-sheng, et al.; "Reduction of motion artifact in pulse oximetry by smoothed pseudo WignerVille distribution," *Journal of NeuroEngineering and Rehabilitation*, vol. 2, No. 3 (9 pages) (Mar. 2005).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

R. Neumann, et al.; "Fourier Artifact suppression Technology Provides Reliable $SpO_2$," *Abstracts*, A11, p. S105. (undated).

* cited by examiner

METHOD FOR ENHANCING PULSE OXIMERY CALCULATIONS IN THE PRESENCE OF CORRELATED ARTIFACTS

CROSS-REFERENCE TO RELATED APPLICATIONS

This application is a continuation of U.S. application Ser. No. 11/072,682, filed Mar. 3, 2005, the disclosure of which is hereby incorporated by reference in its entirety for all purposes.

BACKGROUND

The present invention relates in general to pulse oximetry, and in particular to the processing of signals generated by a pulse oximeter.

A pulse oximeter is typically used to measure various blood characteristics including the blood oxygen saturation of hemoglobin in arterial blood and the pulse rate of the patient. Measurement of these characteristics has been accomplished by use of a non-invasive sensor that passes light through a portion of a patient's blood perfused tissue and photo-electrically senses the absorption and scattering of light in such tissue. The amount of light absorbed and scattered is then used to estimate the amount of blood constituent in the tissue using various algorithms known in the art. The "pulse" in pulse oximetry comes from the time varying amount of arterial blood in the tissue during a cardiac cycle. The signal processed from the sensed optical measurement is the familiar plethysmographic waveform, which corresponds with the cyclic attenuation of optical energy through a portion of a patient's blood perfused tissue.

Various physiological and/or external factors can adversely impact the accuracy and/or the reliability of physiological parameters that are estimated by a pulse oximeter. These undesirable factors are sometimes referred to as artifacts. Artifacts in general and correlated artifacts in particular can be caused by motion, respiratory artifact, or electronic interference. Correlated artifact is an artifact that perturbs more than one of the signals that are provided by an oximeter sensor, and where the perturbations are largely correlated between those signals.

It is desirable for a pulse oximetry system to be able to perform its calculations in the presence of correlated artifacts.

SUMMARY

The present invention provides a pulse oximeter that has the capability of performing calculations in the presence of correlated artifacts. The embodiments of the present invention provide a method of combining the correlated artifacts from multiple signals so as to cancel or reduce the amplitude of the artifact in the combined signal, wherein the weights for the combining are determined by evaluation of pulse shape characteristics in the combined signal.

In one aspect, the present invention provides a method for determining a physiological parameter in the presence of correlated artifact. The method includes obtaining two digital waveforms, x and y, the waveforms being representative of the absorption of two wavelengths of electromagnetic energy received from a blood-perfused tissue, and where each of the waveforms has a component corresponding to a plethysmographic waveform and a component corresponding to the correlated artifact; calculating several weighted difference waveforms of the form x−R*y, where R is a multiplier, by varying R over a range; evaluating the several weighted difference waveforms using a shape characteristic of the weighted difference waveform; identifying a weighted difference waveform most closely representative of the plethysmographic waveform; identifying a weighted difference waveform most different from the plethysmographic waveform; determining a pleth-based physiological parameter using the waveform most closely representative of the plethysmographic waveform; determining at least one artifact-based physiological parameter using the waveform most different from the plethysmographic waveform; and rejecting other possible candidate values for the pleth-based physiological parameter using the artifact-based physiological parameter.

For a fuller understanding of the nature and advantages of the embodiments of the present invention, reference should be made to the following detailed description taken in conjunction with the accompanying drawings.

DETAILED DESCRIPTION OF THE INVENTION

The methods and systems in accordance with the embodiments of the present invention are directed towards enhancing pulse oximetry calculations in the presence of correlated artifact(s). The invention is particularly applicable to and will be explained by reference to measurements of oxygen saturation of hemoglobin in arterial blood and pulse or heart rate, as in pulse oximeter monitors and pulse oximetry sensors.

A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared (IR) signals. This modulation ratio has been observed to correlate well to arterial oxygen saturation. Pulse oximeters and sensors may be empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING," issued Dec. 29, 1998, and U.S. Pat. No. 4,911,167, entitled "METHOD AND APPARATUS FOR DETECTING OPTICAL PULSES," issued Mar. 27, 1990, which are both herein incorporated by reference in their entirety for all purposes. The relationship between oxygen saturation and modulation ratio is described, for example, in U.S. Pat. No. 5,645,059, entitled "MEDICAL SENSOR WITH MODULATED ENCODING SCHEME," issued Jul. 8, 1997, which is herein incorporated by reference in its entirety for all purposes. Most pulse oximeters extract the plethysmographic signal having first determined saturation or pulse rate, both of which are susceptible to interference.

Figure 1:
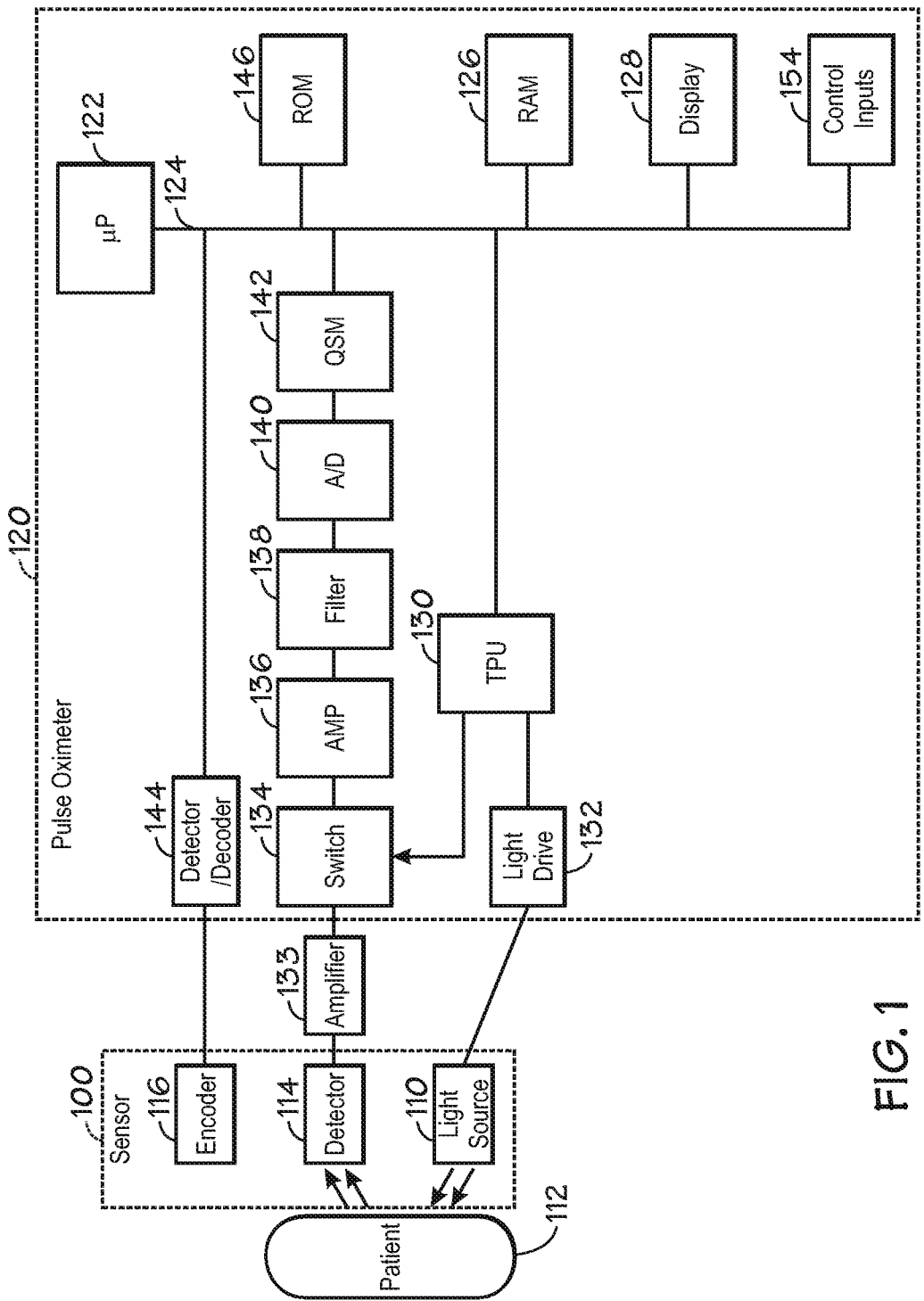
FIG. 1 is a block diagram of an exemplary oximeter.

FIG. 1 is a block diagram of one embodiment of a pulse oximeter that may be configured to implement the embodiments of the present invention. Light from light source 110 passes into a blood perfused tissue 112, and is scattered and detected by photodetector 114. A sensor 100 containing the light source and photodetector may also contain an encoder 116 which provides signals indicative of the wavelength of light source 110 to allow the oximeter to select appropriate calibration coefficients for calculating oxygen saturation. Encoder 116 may, for instance, be a resistor.

Sensor 100 is connected to a pulse oximeter 120. The oximeter includes a microprocessor 122 connected to an internal bus 124. Also connected to the bus are a RAM memory 126 and a display 128. A time processing unit (TPU) 130 provides timing control signals to light drive circuitry 132 which controls when light source 110 is illuminated, and if multiple light sources are used, the multiplexed timing for the different light sources. TPU 130 also controls the gating-in of signals from photodetector 114 through an amplifier 133 and a switching circuit 134. These signals are sampled at the proper time, depending upon which of multiple light sources is illuminated, if multiple light sources are used. The received signal is passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier, filter and A/D converters for multiple light wavelengths or spectra received.

Based on the value of the received signals corresponding to the light received by photodetector 114, microprocessor 122 will calculate the oxygen saturation using various algorithms. These algorithms require coefficients, which may be empirically determined, corresponding to, for example, the wavelengths of light used. These are stored in a ROM 146. In a two-wavelength system, the particular set of coefficients chosen for any pair of wavelength spectra is determined by the value indicated by encoder 116 corresponding to a particular light source in a particular sensor 100. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The brief description of an exemplary pulse oximeter set forth above, serves as a basis for describing the methods for enhancing pulse oximetry calculation in the presence of correlated artifact, which are described below.

Figure 2:
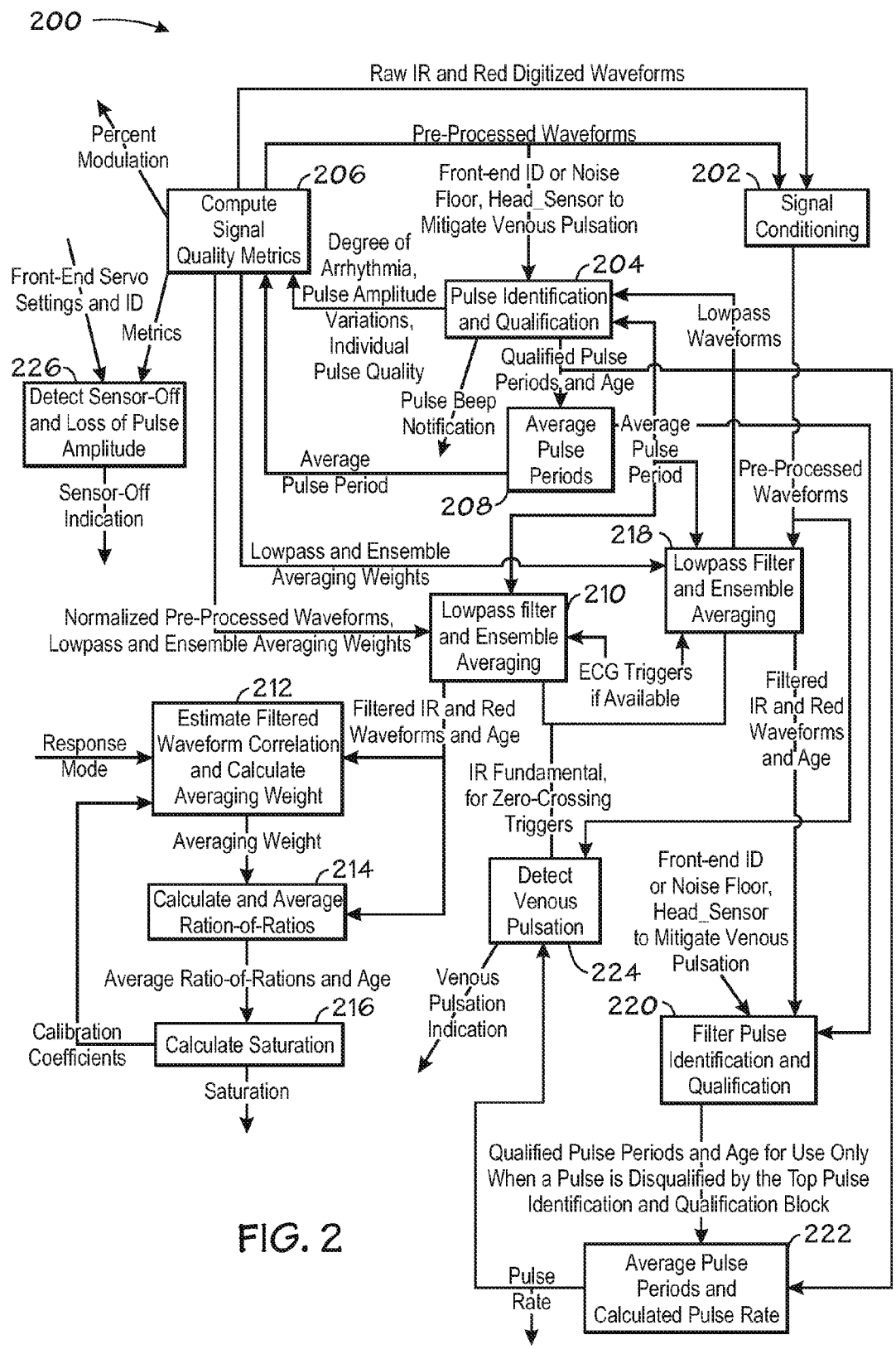
FIG. 2 is a block diagram of the signal processing architecture of a pulse oximeter in accordance with one embodiment of the present invention.

The embodiments of the present invention may be implemented as a part of a larger signal processing system used to process optical signals for the purposes of operating a pulse oximeter. Such a signal processing system is shown in FIG. 2, which is a block diagram 200 of a signal processing architecture of a pulse oximeter in accordance with one embodiment of the present invention. The signal processing architecture 200 in accordance with the embodiments of the present invention may be implemented as a software algorithm that is executed by a processor of a pulse oximeter. In addition to calculating oxygen saturation and pulse rate, the system 200 measures various signal metrics that are used to determine filter weighting coefficients. Signal metrics are things that indicate if a pulse is likely a plethysmograph or noise. Signal metrics may be related to, for example, frequency (is it in the range of a human heart rate), shape (is it shaped like a cardiac pulse), rise time, etc. The system shown in FIG. 2 calculates both the oxygen saturation, and the pulse rate, as well as detecting venous pulsation and sensor off and lost pulse conditions, which are described separately below.

I. Oxygen Saturation Calculation

Block 202 represents the operation of the Signal Conditioning block. The digitized red and IR signals or waveforms are received and are conditioned in this block by: (1) taking the $1^{st}$ derivative to get rid of baseline shift, (2) low pass filtering with fixed coefficients, and (3) dividing by a DC value to preserve the ratio. The function of the Signal Conditioning subsystem is to emphasize the higher frequencies that occur in the human plethysmograph and to attenuate low frequencies in which motion artifact is usually concentrated. The Signal Conditioning subsystem selects its filter coefficients (wide or narrow band) based on hardware characteristics identified during initialization. Inputs to block 202 are digitized red and IR signals, and its outputs are pre-processed red and IR signals.

Block 204 represents the operation of the Pulse Identification and Qualification block. The low pass filtered digitized red and IR signals are provided to this block to identify pulses, and qualify them as likely arterial pulses. This is done using a pre-trained neural network, and is primarily done on the IR signal. The pulse is identified by examining its amplitude, shape and frequency. An input to this block is the average pulse period from block 208. This function changes the upfront qualification using the pulse rate. The output of block 204 indicates the degree of arrhythmia and individual pulse quality. Inputs to block 204 are: (1) pre-processed red and IR signals, (2) Average pulse period, and (3) lowpass waveforms from the low pass filter. Outputs from block 204 include: (1) degree of arrhythmia, (2) pulse amplitude variations, (3) individual pulse quality, (4) pulse beep notification, and (5) qualified pulse periods and age.

Block 206 is used to compute signal quality metrics. This block (block 206) determines the pulse shape (e.g., derivative skew), period variability, pulse amplitude and variability, Ratio of Ratios variability, and frequency content relative to pulse rate. Inputs to block 206 include: (1) raw digitized red and IR signals, (2) degree of arrhythmia, individual pulse quality, pulse amplitude variation, (3) pre-processed red and IR signals, and (4) average pulse period. Outputs from block 206 include: (1) lowpass and ensemble averaging filter weights, (2) metrics for sensor off detector, (3) normalized pre-processed waveforms, and (4) percent modulation.

Block 208 computes average pulse periods. This block (block 208) calculates the average pulse period from the pulses received. Inputs to block 208 include: qualified pulse periods and age. An output from block 208 includes the average pulse period.

Block 210 represents the functioning of the lowpass filter and ensemble averaging subsystem. Block 210 low pass filters and ensemble averages normalized and preprocessed waveforms processed by block 206. The weights for the low pass filter are determined by the Signal Metrics block 206. The signal is also ensemble averaged (this attenuates frequencies other than those of interest near the pulse rate and its harmonics), with the ensemble averaging filter weights also determined by Signal Metrics block 206. Less weight is assigned if the signal is flagged as degraded. More weight is assigned if the signal is flagged as arrhythmic because ensemble-averaging is not appropriate during arrhythmia. Red and IR waveforms are processed separately, but with the same filtering weights. The filtering is delayed (e.g., approximately one second) to allow the signal metrics to be calculated first.

The filters use continuously variable weights. If samples are not to be ensemble-averaged, then the weighting for the previous filtered samples is set to zero in the weighted average, and the new samples are still processed through the signal processing algorithm. This block tracks the age of the signal and/or the accumulated amount of filtering (e.g., sum of response times and delays in processing). Too old a result will be flagged, if good pulses haven't been detected for a while. The inputs to block 210 include: (1) normalized pre-processed red and IR signals, (2) average pulse period, (3) low pass filter weights and ensemble averaging filter weights, (4) ECG triggers, if available, and (5) IR fundamental, for zero-crossing triggers. Outputs from block 210 include: (1) filtered red and IR signals, and (2) age.

Block 212 represents operations that estimate the ratio-of-ratios variance for the filtered waveforms and calculate averaging weights. The variable weighting for the filter is controlled by the ratio-of-ratios variance. The effect of this variable-weight filtering is that the ratio-of-ratios changes slowly as artifact increases and changes quickly as artifact decreases. The subsystem has two response modes, including fast and normal modes. For example, filtering in the fast mode targets an age metric of 3 seconds, and the target age may be 5 seconds in the normal mode. In the fast mode, the minimum weighting of the current value is clipped at a higher level. In other words, a low weight is assigned to the newest ratio-of-ratios calculation if there is noise present, and a high weight if no noise is present. The inputs to block 212 include: (1) filtered red and IR signals and age, (2) calibration coefficients, and (3) response mode (e.g., user speed settings). Outputs from block 212 include an averaging weight for ratio-of-ratios calculation. The averaging weight is used as an input to block 214 along with filtered IR and Red waveforms to calculate averaged ratio of ratios and age.

Block 216 represents operations that calculate oxygen saturation. Saturation is calculated using an algorithm with the calibration coefficients and averaged ratio of ratios. Inputs to block 116 include: (1) Averaged Ratio-of-Ratios, and (2) calibration coefficients. An output from block 216 is the oxygen saturation value.

II. Pulse Rate Calculation

Block 218 low pass filters and ensemble averages the signal(s) conditioned by block 202, for the pulse rate identification. The weights for the low pass filter are determined by the Signal Metrics block 206. The signal is also ensemble averaged (this attenuates frequencies other than those of interest near the pulse rate and its harmonics), with the ensemble averaging filter weights also determined by Signal Metrics block 206. Less weight is assigned if the signal is flagged as degraded. More weight is assigned if the signal is flagged as arrhythmic because ensemble-averaging is not appropriate during arrhythmia. Red and IR are processed separately, but with the same filtering weights. The filtering is delayed (e.g., approximately one second) to allow the signal metrics to be calculated first.

The filters use continuously variable weights. If samples are not to be ensemble-averaged, then the weighting for the previous filtered samples is set to zero in the weighted average, and the new samples are still processed through the signal processing algorithm. This block (block 218) tracks the age of the signal and/or the accumulated amount of filtering (sum of response times and delays in processing). Too old a result will be flagged (if good pulses haven't been detected for awhile). Inputs to block 218 include: (1) pre-processed red and IR signals, (2) average pulse period, (3) lowpass filter weights and ensemble averaging filter weights, (4) ECG triggers, if available, and (5) IR fundamental, for zero-crossing triggers. Outputs from block 218 include: (1) filtered red and IR signals and (2) age.

Block 220, or the Filtered Pulse Identification and Qualification block, calculates the pulse periods from the filtered waveforms, and its results are used only when a pulse is disqualified by block 204. Inputs to block 220 include: (1) filtered red and IR signals and age, (2) average pulse period, (3) front end ID or noise floor, (4) and the kind or type of sensor that is used to detect the IR and Red energies. Output from block 220 includes qualified pulse periods and age.

Block 222, or the Average Pulse Periods and Calculate Pulse Rate block, calculates the pulse rate and average pulse period. This block (block 222) receives qualified pulse periods and age as inputs and provides (1) average pulse period and (2) pulse rate as outputs.

III. Venous Pulsation

Block 224, or the Detect Venous Pulsation block receives as inputs the pre-processed red and IR signals and age from Block 202, and pulse rate and provides an indication of venous pulsation as an output. Block 224 also provides an IR fundamental waveform in the time domain using a single-tooth comb filter which is output to the Ensemble Averaging filters (e.g., block 210 and 218). Inputs to block 224 include: (1) filtered red and IR signals and age and (2) pulse rate. Outputs from block 124 include: an indication of venous pulsation and IR fundamental. In one embodiment, block 224 measures the "openness" of an IR-Red Lissajous plot to determine the whether a flag (e.g., Venous_Pulsation) should be set. The output flag (e.g., Venous_Pulsation) is updated periodically (e.g., every second). In addition, the IR fundamental waveform is output to the Ensemble Averaging filters.

IV. Sensor Off

Block 226, or the Detect Sensor-Off and Loss of Pulse Amplitude block, uses a pre-trained neural net to determine whether the sensor is off the surface of the blood-perfused tissue, for example, of a patient. The inputs to the neural net are metrics that quantify several aspects of the behavior of the IR and Red values over the last several seconds. Samples are ignored by many of the system 200's subsystems while the signal state is either not indicative of a pulse being present, or indicative that a sensor is not on a monitoring site (e.g., Pulse Present, Disconnect, Pulse Lost, Sensor May be Off, and Sensor Off). Inputs to block 226 include: (1) signal quality metrics, and (2) the oximeter's LED brightness, amplifier gain, and (3) an ID indicating the oximeter's hardware configuration. Outputs from block 226 include a signal state including sensor-off indication.

In the architecture 200 described above, the function of block 226, Pulse lost and Pulse Search indications, may be derived using information from several parts of the signal processing architecture. In addition, the signal processing architecture will not use the received IR and red waveforms to compute oxygen saturation or pulse rate if a valid sensor is not connected, or if the Sensor-Off or Loss of Pulse Amplitude are detected by the signal processing architecture.

The brief description of an embodiment of a pulse oximeter signal processing architecture in accordance with the present invention, set forth above, serves as a basis for describing the enhanced pulse oximetry calculations in the presence of correlated artifact(s), as is generally depicted by blocks 216 and 222 above.

Figure 3:
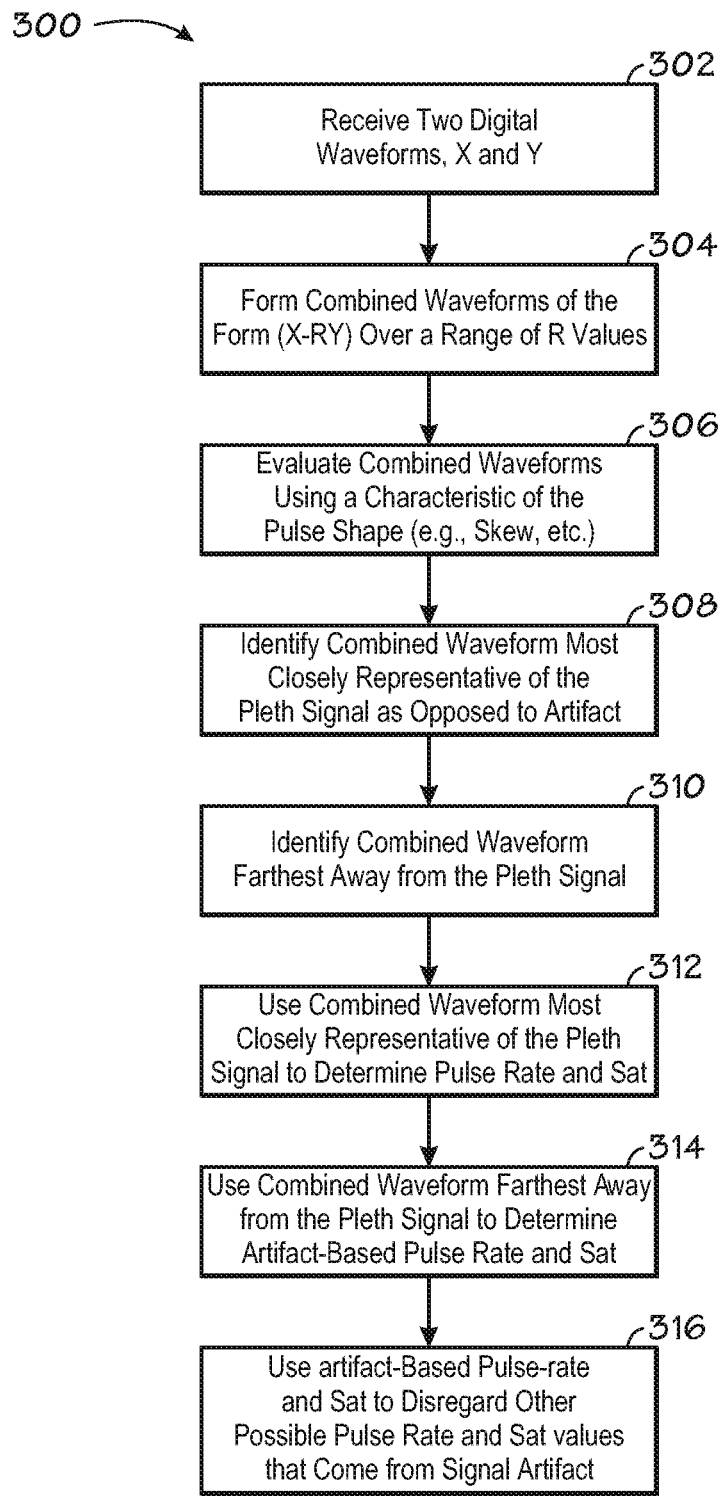
FIG. 3 is a block diagram of the signal processing architecture of a pulse oximeter in accordance with one embodiment of the present invention for performing calculations in the presence of correlated artifacts.

FIG. 3 is a block diagram 300 of the signal processing architecture of a pulse oximeter in accordance with one embodiment of the present invention for performing enhanced saturation and/or pulse rate calculations in the presence of correlated artifacts. It should be realized that the operations depicted by the diagram 300 need not be carried out in the order shown in FIG. 3. A person skilled in the art of pulse oximetry signal processing will realize that the operations of FIG. 3 may be carried out in any order, or that steps may be combined, or even skipped. These various permutations of the operation in accordance with the diagram of FIG. 3 are also within the scope of the present methodology. In general, the block diagram 300 shows that in block 302, two digitized waveforms X and Y are received. In block 304, the two waveforms are combined to form a weighted difference waveform having the form X−R*Y, where R is a multiplier. The value of R is varied and thus a series of weighted difference waveforms are formed. In block 306, the combined waveforms are evaluated using a characteristic of the pulse shape. For example, one such pulse shape characteristic is the skew of the combined waveform. In blocks 308 and 310, the combined waveform most closely representative of a plethysmograph and the waveform least representative of a plethysmograph are identified. Having identified these two waveforms (i.e., most and least representative), the most representative waveforms is used to determine pulse rate and/or oxygen saturation (block 312). Also, the least representative waveform may optionally be used to determine an artifact-based pulse rate and/or oxygen saturation (block 314), and the artifact-based estimates of pulse rate and/or oxygen saturation may optionally be used to disregard other possible estimates of pulse rate and/or oxygen saturation (block 316).

The operation of diagram 300 is described in further detail below. The method for enhancing saturation and/or pulse rate calculation in the presence of correlated artifact, includes the following steps, namely:

1. Calculating two or more digital waveforms, where the two waveforms correspond to the absorption of two or more wavelengths of electromagnetic energy received from a pulsatile tissue bed;

2. Filtering the waveforms to emphasize one or more characteristic of the pulse shape that differentiates the waveform from correlated artifact. For example, applying a first difference filter to a normal or typical human plethysmograph produces a filtered waveform with a skewness between −1 and −2 in most subjects, whereas applying the same filter to a motion artifact signal produces a filtered waveform with a near-zero skewness.

3. Calculating multiple weighted differences between the filtered waveforms, X and Y, of the form X−R*Y.

4. Varying R over a range such that some value of R results in a weighted difference waveform that minimizes the correlated artifact.

5. Calculating the skewness or other shape characteristic of the weighted difference waveforms over an appropriate time interval (e.g., at least one pulse period).

6. Selecting the value of R that produces a weighted difference waveform having a shape that is least characteristic of a pulse. This waveform most closely resembles the artifact.

7. Calculating a saturation value using the waveform of "6" above.

8. Using the saturation value of "7" above for selecting from among multiple saturation estimates calculated by other saturation calculation algorithms.

9. Calculating saturation from the two or more filtered waveforms, but excluding those components contained in the weighted difference waveform having a shape that is least characteristic of a pulse. The exclusion operation may be performed in various ways. For example, the strongest one or more frequencies contained in the least characteristic weighted difference waveform may be the excluded frequencies. Alternatively, the least characteristic waveform (i.e. per "6" above) may be canceled from the two or more filtered waveforms using a cancellation filter.

10. Selecting the weighted difference waveform of "6" above having a skew that is most characteristic of a pulse.

11. Using the weighted difference waveform of "10" above to calculate a pulse rate.

12. Calculating oxygen saturation using the waveform of "10" above and using only those components of the waveform used for calculating the pulse rate. For example, the useful components may be isolated in a manner similar to the exclusion operation of "9" above.

13. Calculating the skewness or other shape characteristic of the weighted difference waveforms over an appropriate time interval (e.g., at least one pulse period), wherein the total absolute difference in skewness between multiple consecutive values over a selected range of R is used as a measure of the complexity of the pulse oximetry signal, where overly complex signals are rejected as unsuitable for oxygen saturation and/or pulse rate calculation.

14. Combining "13" above, and wherein the measure of complexity is applied to other metrics, such as for example, energy, corresponding to the selected range of R, where overly complex signals are rejected as unsuitable for oxygen saturation and/or pulse rate calculation.

The operation of the enhanced signal processing in accordance with the embodiments of the present invention, which is generally described in conjunction with FIG. 3 above, is further described below in conjunction with FIGS. 4-7.

Figure 4:
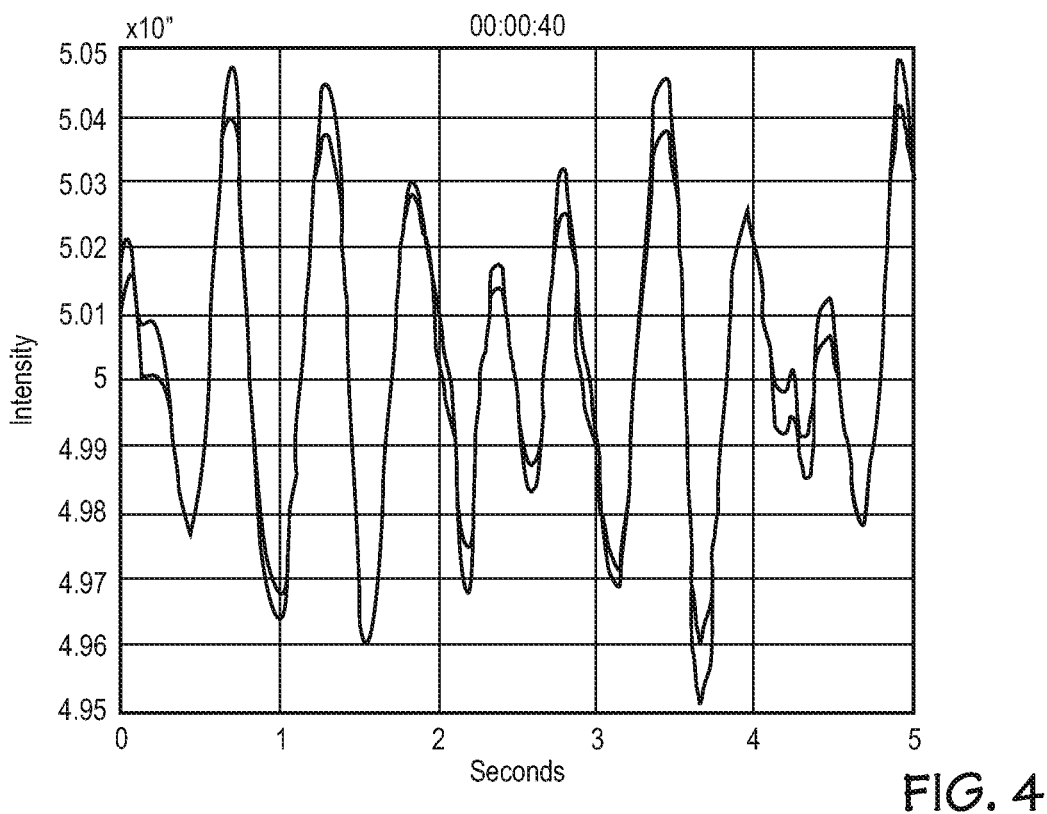
FIG. 4 is an exemplary graph of IR and Red plethysmograph at a saturation of approximately 94 percent, shown corrupted with a sinusoidal artifacts of equal magnitudes in both channels, which artifacts would yield a saturation of approximately 80 percent.

FIG. 4 is an exemplary graph of IR and Red plethysmograph at a saturation of approximately 94 percent, shown corrupted with a sinusoidal artifacts of equal magnitudes in both channels, which artifacts would yield a saturation of approximately 80 percent.

Figure 5:
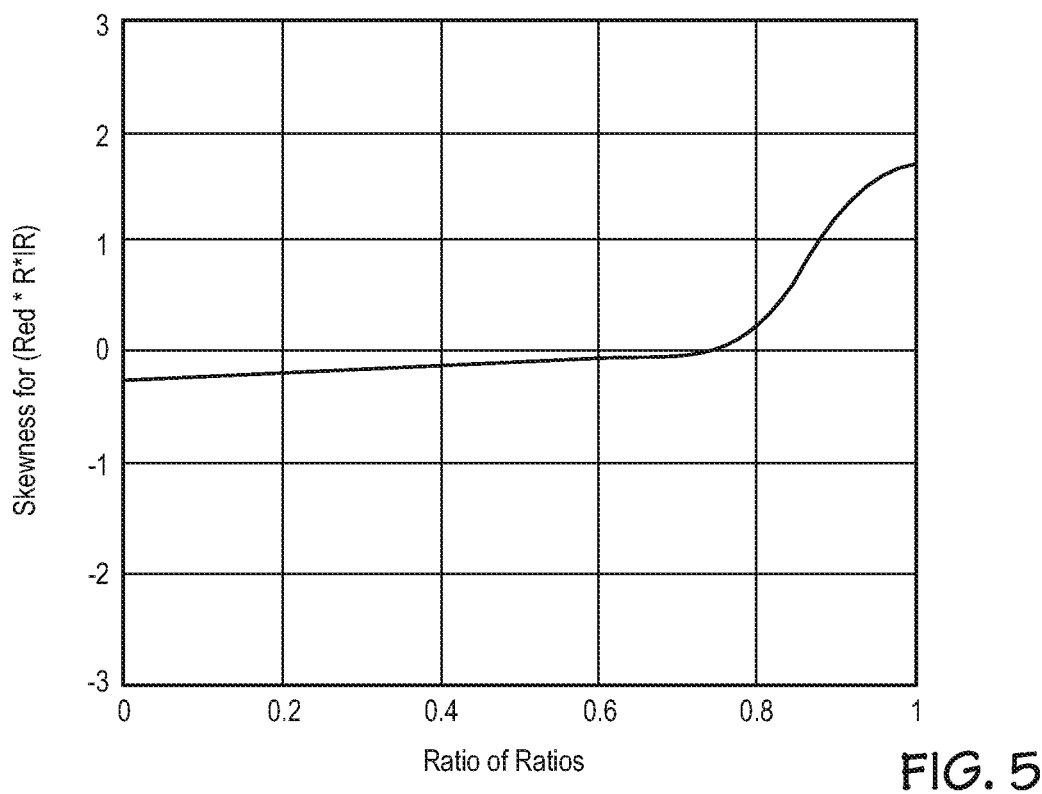
FIG. 5 is an exemplary graph of skewness of the weighted difference signal.

FIG. 5 is an exemplary graph of skewness of the weighted difference signal.

Figure 6:
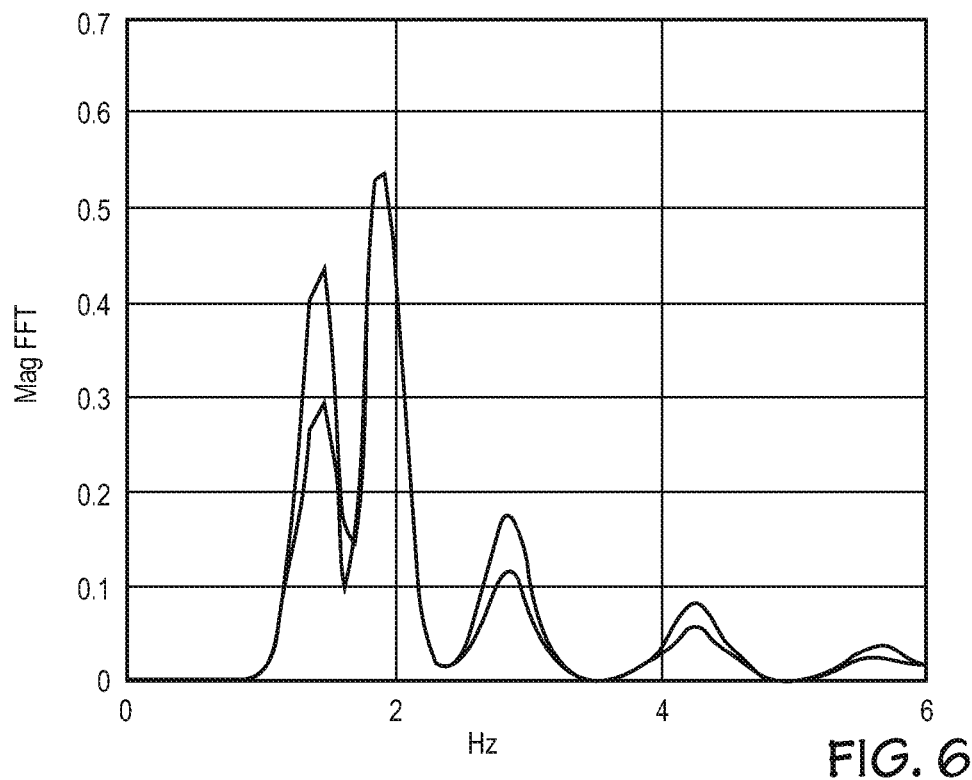
FIG. 6 is an exemplary FFT graph of IR and Red plethysmograph, reflecting a pulse rate of approximately 85 beats per minutes ("BPM"), with harmonics, and a 115 BPM sinusoid.

FIG. 6 is an exemplary FFT graph of IR and Red plethysmograph, reflecting a pulse rate of approximately 85 beats per minutes ("BPM"), with harmonics, and a 115 BPM sinusoid.

Figure 7:
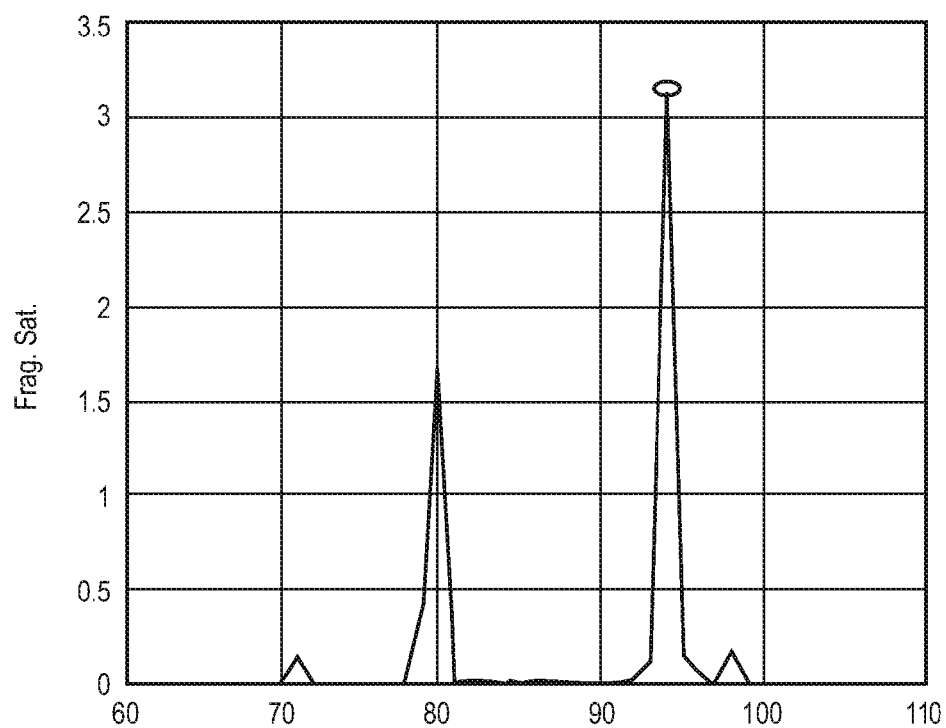
FIG. 7 is an exemplary frequency domain histogram of saturation (vs. pulse rate) values obtainable by one of multiple methods. The histogram reflects two potential saturation estimates, one at approximately 80 percent (artifact) and the other at 95 percent (pulse).

FIG. 7 is an exemplary frequency domain histogram of saturation (vs. pulse rate) values obtainable by one of multiple methods. The histogram reflects two potential saturation estimates, one at approximately 80 percent (artifact) and the other at 95 percent (pulse).

In FIG. 5, the weighted difference waveform (Red−R*IR) having a skewness least-characteristic of a pulse (i.e. zero skewness) occurs for R of approximately 0.7, or a saturation value of approximately 92 percent, which corresponds with the saturation estimate that is made using the method of step 7 above. In step 8, this value of R is used to select the saturation value of 94 percent from the saturation histogram of FIG. 7, and not the possible saturation value of 80 percent (from the saturation histogram of FIG. 7). Using the complexity metrics described in step 13 (i.e., the skewness graph of FIG. 5) and step 14 (for the saturation histogram of FIG. 7) both indicate that the IR and Red waveforms are suitable for pulse oximetry calculations, containing only two primary components, of which only one has a characteristic pulse shape.

In FIG. 5, the weighted difference waveform (Red−R*IR) having a skewness most-characteristic of a pulse (i.e., a very non-zero skewness) occurs for R of approximately 0.1, which resulting weighted difference waveform is the inversion of the plethysmograph, and no artifact. This most characteristic waveform may be used to reliably calculate pulse rate in "11," above. In addition, a filter may be used to extract the components of the most-characteristic waveform from the two or more waveforms of "2" above, for use in saturation calculation per "12" above.

In some embodiments of the present invention, pulse shape metrics other than the skewness may be used for the processing of the waveforms. These other metrics include various signal quality metrics described above in conjunction with Block 206 of FIG. 2. In particular, other pulse shape metrics may include: the pulse shape (e.g., derivative skew), period variability, pulse amplitude and variability, Ratio of Ratios variability, and frequency content relative to pulse rate, degree of arrhythmia, individual pulse quality, pulse amplitude variation, the degree of similarity or correlation between the two waveforms, the degree of motion artifact by obtaining a ratio of a current pulse amplitude to the long-term average pulse amplitude of said signals, a ratio of a current pulse amplitude to the previous pulse amplitude, and a ratio of a current pulse period to that of an average pulse period. In addition, other pulse shape metrics such as, the "MIN-MAX-MIN" and the "PATH LENGTH" pulse shape indicators, may also be used.

The "MIN-MAX-MIN" indicator provides for a measure of the arterial pulse shape. The arterial pulse referred to herein is caused by a cardiac cycle commonly referred to a heartbeat. During a typical cardiac cycle, blood pressure rises from a minimum value (MIN) at diastole to a maximum (MAX) at systole. The "MIN-MAX-MIN" indicator is a ratio represented by a fraction having the time it takes the pulse to go from a MAX to a MIN as the numerator and having the time it takes the pulse to go from a MIN to a MAX as the denominator. This indicator provides an indication of the ratio of fall to rise times of arterial pulse. A fundamental fact of human physiology is that in a typical arterial pulse, it takes a shorter time to go from the diastole to systole (MIN to MAX) than it does to go from systole to diastole (MAX to MIN). Recognizing this fundamental physiological aspect, then if the "MIN-MAX-MIN" indicator shows that for a pulse, the rise time is bigger than the fall time, then this indicates that the sensor's light is being modulated by other than an arterial pulse. The inventor herein has identified that when a pulse's rise time is bigger than its fall time, the light is not modulated by pulsation of evenly distributed arterial blood, but it is most likely that the observed pulse-like phenomenon is due to throbbing of underlying large blood vessels or physical movement of the sensor. It is known that either of these mechanisms may cause large errors in the calibration of the resulting oxygen saturation estimate. Therefore, by analyzing the shape of the arterial pulse, the "MIN-MAX-MIN" indicator determines whether the light modulation is due to a pulsation, or evenly distributed arterial blood, or other phenomenon such as motion.

The "PATH LENGTH" indicator is also indicative of the pulse shape. This indicator provides for a measure of the frequency content of the pulse waveform relative to the pulse rate. While many algorithms may be used to compute "PATH LENGTH," one equation that may be used to compute it is as follows:

$$PathLength = \frac{\sum_{i=0}^{i=Samples\_in\_Pulse-1} |IR_{t-i} - IR_{t-i-1}|}{Pulse\_Max - Pulse\_Min}$$

High values of this metric indicate that a high proportion of the energy in the pulse is at frequencies higher than the pulse rate. High frequency components in the arterial pulse shape are an indication that light is being modulated by other than arterial pulsations. These high frequency components are also most likely to be caused by movement of the sensor. As described above, it is known that physical movement is a source of error when estimating blood oxygen saturation in pulse oximeters. Therefore, the "PATH LENGTH" indicator, is also a motion and/or pulse shape indicator, which is used to infer that signals that have high frequency components often lead to inaccurate estimates of pulse rate and/or blood oxygen saturation.

Accordingly, as will be understood by those of skill in the art, the present invention which is related to enhancing pulse oximetry calculations in the presence of correlated artifact(s), may be embodied in other specific forms without departing from the essential characteristics thereof. For example, while some aspects of the present embodiments have been described in the time-domain, frequency-based methods are equally relevant to the embodiments of the present invention. Accordingly, the foregoing disclosure is intended to be illustrative, but not limiting, of the scope of the invention, which is set forth in the following claims.

What is claimed is:

1. A method comprising:
receiving two waveforms corresponding to two different wavelengths of light from a patient;
combining the two waveforms to form a plurality of weighted difference waveforms, wherein the plurality of weighted difference waveforms vary from one another by a value of a multiplier;
identifying one of the weighted difference waveforms from the plurality of weighted difference waveforms using a characteristic of one or more of the plurality of weighted difference waveforms; and
calculating a physiological parameter based at least in part on the identified weighted difference waveform.

2. The method of claim 1, wherein the physiological parameter comprises a pulse rate.

3. The method of claim 1, wherein the physiological parameter comprises an oxygen saturation value.

4. The method of claim 1, wherein identifying one of the weighted difference waveforms from the plurality of weighted difference waveforms comprises identifying the waveform that most closely resembles a plethysmographic waveform.

5. The method of claim 1, wherein identifying one of the weighted difference waveforms from the plurality of weighted difference waveforms comprises identifying the waveform that least closely resembles a plethysmographic waveform.

6. The method of claim 1, comprising identifying another one of the weighted difference waveforms from the plurality of weighted difference waveforms using another characteristic of one or more of the plurality of weighted difference waveforms, and wherein calculating the physiological parameter is based at least in part on the another identified weighted difference waveform.

7. The method of claim 1, wherein the characteristic of one or more of the plurality of weighted difference waveforms comprises at least one of a measure of complexity of one or more of the plurality of weighted difference waveforms or a measure of skew of one or more of the plurality of weighted difference waveforms.

8. A pulse oximeter, comprising:
a processor capable of:
receiving two waveforms corresponding to different wavelengths of light from a patient;
combining the two received waveforms to form a plurality of weighted difference waveforms, wherein the plurality of weighted difference waveforms vary from one another by a value of a multiplier;
identifying one of the weighted difference waveforms from the plurality of weighted difference waveforms using a characteristic of one or more of the plurality of weighted difference waveforms; and
calculating a physiological parameter based at least in part on the identified weighted difference waveform.

9. The oximeter of claim 8, wherein identifying one of the weighted difference waveforms from the plurality of weighted difference waveforms comprises identifying the waveform that most closely resembles a plethysmographic waveform.

10. The oximeter of claim 8, wherein identifying one of the weighted difference waveforms comprises identifying the waveform that least closely resembles a plethysmographic waveform.

11. The oximeter of claim 8, wherein the processor is capable of identifying another one of the weighted difference waveforms from the plurality of weighted difference waveforms using another characteristic of one or more of the plurality of weighted difference waveforms, and wherein calculating the physiological parameter is based at least in part on the another identified weighted difference waveform.

12. The oximeter of claim 8, wherein the characteristic of one or more of the plurality of weighted difference waveforms comprises a measure of complexity of one or more of the plurality of weighted difference waveforms.

13. The oximeter of claim 8, wherein the characteristic of one or more of the plurality of weighted difference waveforms comprises a measure of skew of one or more of the plurality of weighted difference waveforms.

14. The oximeter of claim 8, wherein the characteristic of one or more of the plurality of weighted difference waveforms comprises at least one of a measure of the degree of arrhythmia of one or more of the plurality of weighted difference waveforms or a measure of the degree of similarity or correlation between two or more of the plurality of weighted difference waveforms.

15. The oximeter of claim 8, wherein the characteristic of one or more of the plurality of weighted difference waveforms comprises at least one of: a measure of the degree of noise by obtaining a ratio of a current pulse amplitude to the long-term average pulse amplitude of one or more of the plurality of weighted difference waveforms; a ratio of a current pulse amplitude to a previous pulse amplitude of the one or more of the plurality of weighted difference waveforms; or a ratio of a current pulse period to that of an average pulse period of one or more of the plurality of weighted difference waveforms.

16. The oximeter of claim 8, wherein the characteristic of one or more of the plurality of weighted difference waveforms comprises at least one of a measure of kurtosis of one or more of the plurality of weighted difference waveforms or a measure of a dicrotic notch of one or more of the plurality of weighted difference waveforms.

17. The oximeter of claim 8, wherein the characteristic of one or more of the plurality of weighted difference waveforms comprises a measure of a total absolute change between the two or more plurality of weighted difference waveforms, normalized by a pulse amplitude.

18. A pulse oximetry system comprising:
a sensor capable of detecting two electromagnetic radiation signals corresponding to different wavelengths of light; and
a processor capable of:
receiving two waveforms corresponding to the different wavelengths of light from the sensor;
combining the two waveforms to form a plurality of weighted difference waveforms, wherein the plurality of weighted difference waveforms vary from one another by the value of a multiplier;
identifying at least one of the weighted difference waveforms from the plurality of weighted difference waveforms using at least one characteristic of one or more of the plurality of weighted difference waveforms; and
calculating a physiological parameter based at least in part on the at least one identified weighted difference waveform.

19. The system of claim 18, wherein identifying at least one of the weighted difference waveforms from the plurality of weighted difference waveforms comprises identifying at least one of the waveform that most closely resembles a plethysmographic waveform or the waveform that lease closely resembles a plethysmographic waveform.

20. The system of claim 18, wherein the characteristic of one or more of the plurality of weighted difference waveforms comprises at least one of: a measure of complexity of one or more of the plurality of weighted difference waveforms; a measure of skew of one or more of the plurality of weighted difference waveforms; a measure of the degree of arrhythmia of one or more of the plurality of weighted difference waveforms; a measure of the degree of similarity or correlation between two or more of the plurality of weighted difference waveforms; a measure of the degree of noise by obtaining a ratio of a current pulse amplitude to the long-term average pulse amplitude of one or more of the plurality of weighted difference waveforms; a ratio of a current pulse amplitude to a previous pulse amplitude of the one or more of the plurality of weighted difference waveforms; a ratio of a current pulse period to that of an average pulse period of one or more of the plurality of weighted difference waveforms; a measure of kurtosis of one or more of the plurality of weighted difference waveforms; a measure of a dicrotic notch of one or more of the plurality of weighted difference waveforms; or a measure of a total absolute change between the two or more plurality of weighted difference waveforms, normalized by a pulse amplitude.

* * * * *